United States Patent
Schwartz et al.

(10) Patent No.: US 11,151,738 B2
(45) Date of Patent: Oct. 19, 2021

(54) SCANNING DEVICE WITH IMAGING AND PRESSURE-SENSING FUNCTIONALITY

(71) Applicant: Aetrex Worldwide, Inc., Teaneck, NJ (US)

(72) Inventors: Laurence I Schwartz, New York, NY (US); Kumar Rajan, Clinton, NJ (US); Anthony Yezzi, Smyrna, GA (US)

(73) Assignee: Aetrex Worldwide, Inc., Teaneck, NJ (US)

( * ) Notice: Subject to any disclaimer, the term of this patent is extended or adjusted under 35 U.S.C. 154(b) by 0 days.

(21) Appl. No.: 17/143,878

(22) Filed: Jan. 7, 2021

(65) Prior Publication Data

US 2021/0279900 A1 Sep. 9, 2021

Related U.S. Application Data

(60) Provisional application No. 63/108,067, filed on Oct. 30, 2020, provisional application No. 62/986,502, filed on Mar. 6, 2020.

(51) Int. Cl.
| | | |
|---|---|---|
| *G06T 7/55* | (2017.01) | |
| *G06T 7/00* | (2017.01) | |
| *G01B 21/18* | (2006.01) | |

(52) U.S. Cl.
CPC ............... *G06T 7/55* (2017.01); *G01B 21/18* (2013.01); *G06T 7/0012* (2013.01); *G06T 2207/30004* (2013.01)

(58) Field of Classification Search
None
See application file for complete search history.

(56) References Cited

U.S. PATENT DOCUMENTS

| | | | |
|---|---|---|---|
| 7,493,230 B2 | 2/2009 | Schwartz et al. | |
| 9,402,567 B2 | 8/2016 | Danenberg et al. | |
| D833,307 S | 11/2018 | Nord | |
| 10,417,772 B2 | 9/2019 | Schwartz | |
| 10,463,257 B2 | 11/2019 | Schwartz | |
| 10,492,712 B2* | 12/2019 | Schwartz | G16H 50/50 |
| 2007/0245504 A1* | 10/2007 | Spector | A61B 5/1036 |
| | | | 12/142 N |
| 2010/0157388 A1* | 6/2010 | Pishdadian | G01B 11/24 |
| | | | 358/488 |
| 2017/0272728 A1* | 9/2017 | Rafii | H04N 13/239 |
| 2017/0287992 A1* | 10/2017 | Kwak | H01L 27/3234 |

(Continued)

FOREIGN PATENT DOCUMENTS

| | | |
|---|---|---|
| CN | 108113120 A | 6/2018 |
| CN | 110179468 A | 8/2019 |

(Continued)

OTHER PUBLICATIONS

Lunscher et al., "Foot Depth Map Point Cloud Completion using Deep Learning with Residual Blocks," Journal of Computational Vision and Imaging Systems, 2017, 3 pages.

(Continued)

*Primary Examiner* — Nancy Bitar
(74) *Attorney, Agent, or Firm* — Lowenstein Sandler LLP

(57) ABSTRACT

Embodiments of the present disclosure relate to a scanning device comprising a support base, a pressure panel disposed on an upper surface of the support base, and a plurality of cameras distributed around an outer perimeter of the support base.

18 Claims, 10 Drawing Sheets

(56) References Cited

U.S. PATENT DOCUMENTS

2019/0130822 A1*  5/2019  Jung .................... H01L 27/3227
2019/0150791 A1*  5/2019  Schwartz ............. A61B 5/1038
2020/0060580 A1*  2/2020  Miller .................. A61B 5/1074

FOREIGN PATENT DOCUMENTS

CN        111127625      *   5/2020
EP          1980224 A2      10/2008

OTHER PUBLICATIONS

International Search Report and Written Opinion for PCT/US2021/021047 dated Jun. 11, 2021, 15 pgs.

* cited by examiner

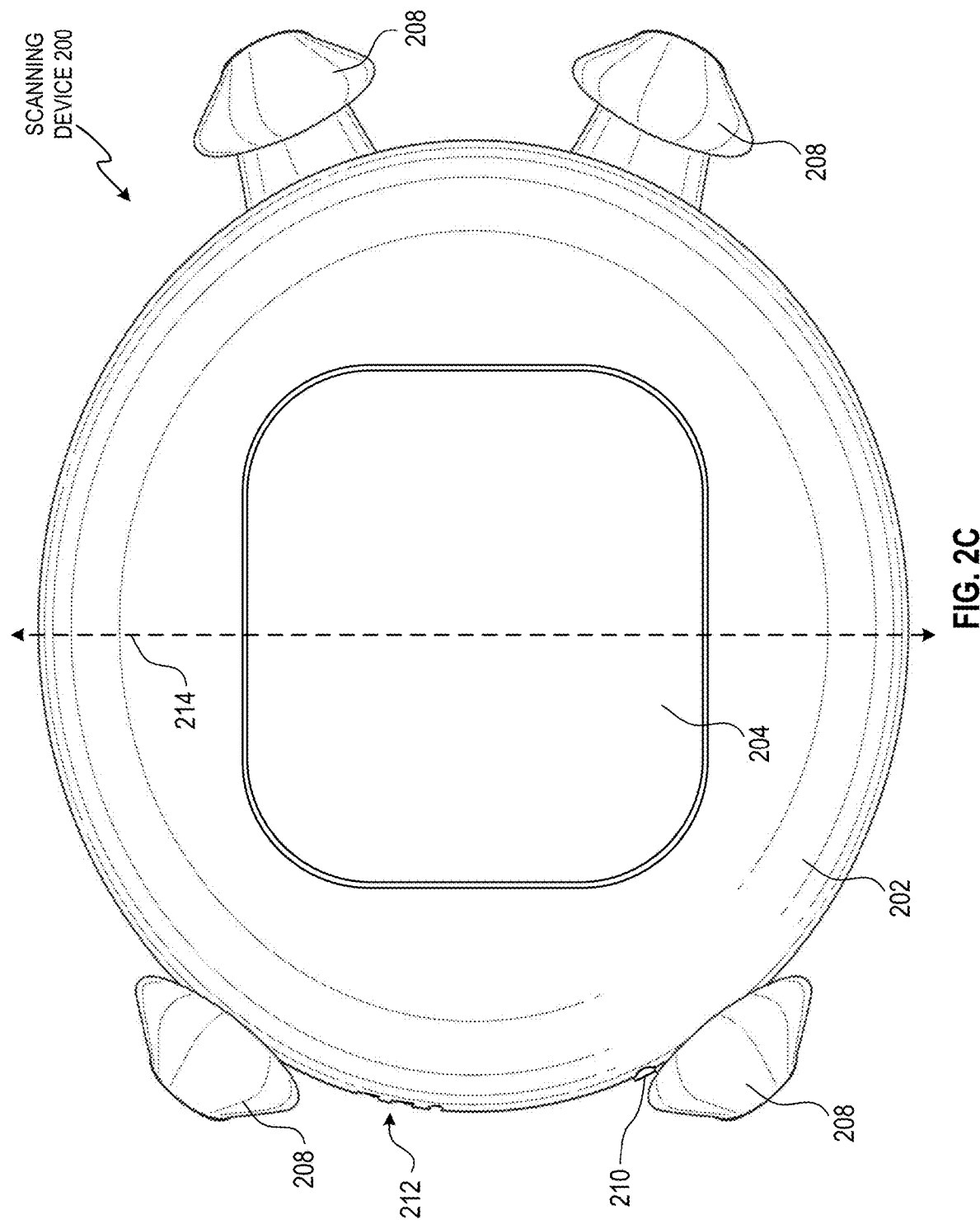

SCANNING DEVICE WITH IMAGING AND PRESSURE-SENSING FUNCTIONALITY

CROSS-REFERENCE TO RELATED APPLICATION(S)

The present application claims the benefit of priority of U.S. Provisional Patent Application No. 62/986,502, filed on Mar. 6, 2020, and U.S. Provisional Patent Application No. 63/108,067, filed on Oct. 30, 2020, the disclosures of which are hereby incorporated by reference herein in their entireties.

TECHNICAL FIELD

The present disclosure relates to the field of customized orthotic devices, and more particularly, to scanning devices used in connection with the production of customized orthotic devices or recommendations of orthotic devices.

BACKGROUND

Foot problems and the corresponding costs associated with foot care are significant in the United States and elsewhere. In cases where the foot problem is debilitating for particular activities, a number of hours of work time can be lost. Foot problems can arise from medical conditions, work conditions requiring standing or walking, athletic activities, and the like. Thus, foot problems can develop from medical conditions, work activity, or leisure activity.

Pedorthics is the field concerned with the design, manufacture, fit, and modification of footwear, foot orthotics, and foot devices as prescribed to help relieve painful or disabling conditions of the foot. The goal of pedorthics is to provide protection and comfort to the consumer/patient, which has been achieved primarily by developing orthotic devices capable of reducing pressure at the greatest areas of impact. Recently, additive manufacturing technologies have been used to produce custom orthotic devices or insoles in lieu of traditional subtractive manufacturing techniques and injection molding. Techniques, such as pressure sensing or imaging, have been used to compute three-dimensional (3D) models of the foot, which serve as the basis for generating customized orthotic devices with additive manufacturing or suggesting recommended pre-fabricated orthotic devices.

BRIEF DESCRIPTION OF THE DRAWINGS

In order to facilitate a fuller understanding of the present disclosure, reference is now made to the accompanying drawings, in which like elements are referenced with like numerals. These drawings should not be construed as limiting the present disclosure, but are intended to be exemplary only.

FIG. 2C shows a top view of the exemplary scanning device in accordance with embodiments of the present disclosure.

DETAILED DESCRIPTION

Described herein are embodiments of a scanning device capable of capturing two-dimensional pressure maps of an individual's foot or feet using a pressure panel while also capturing images of the user's foot or feet from different angles with a plurality of cameras. The scanning device is further capable of enabling dynamic gait analysis by capturing a series of pressure maps of underfoot pressure when the individual steps onto and/or off of the scanning device. In at least one embodiment, the scanning device, or a separate device, performs a 3D reconstruction of the individual's foot or feet based on the pressure map (representative of the bottom of the foot) and the images captured at various angles (representative of the top, front, side, and back views of the foot).

In at least one embodiment, the cameras are evenly distributed around a perimeter of the scanning device. In at least one embodiment, the cameras are unevenly distributed. For example, in an embodiment where only four cameras are used, the cameras may be arranged to define the four corners of a rectangle while being oriented toward a center of the pressure panel (i.e., toward the individual's foot or feet).

In at least one embodiment, the scanning device may enable during gait analysis by capturing pressure data for the user's foot or feet, for example at 5-10 second intervals as the user steps into, across, and/or out of the scanning device. The data may be processed to generate a video showing the evolution of underfoot pressure over time.

Certain embodiments of the present disclosure are also directed to methods utilizing geometric partial differential equations to generate a 3D surface representative of a foot. The method can advantageously compute the 3D model using depth images obtained from the cameras in conjunction with an underfoot pressure map so as to account for the underside of the foot which is not visible to the cameras.

In the description that follows, reference is made to the analysis of an individual's feet for the purpose of generating orthotic devices. It is to be understood that the embodiments described herein are not limited to use in any one particular application and that changes may be made to the disclosed embodiments without departing from the spirit and scope of the disclosure. Although the present disclosure has been described herein in the context of foot orthotics, those of ordinary skill in the art will recognize that its usefulness is not limited thereto and that the present disclosure may be beneficially implemented in connection with the generation of orthotics for other body parts as well. Moreover, the embodiments described herein are not limited to measurements that require both imaging and pressure sensing. Embodiments utilizing imaging exclusively or pressure sensing exclusively are also contemplated.

System Architecture

Figure 1:
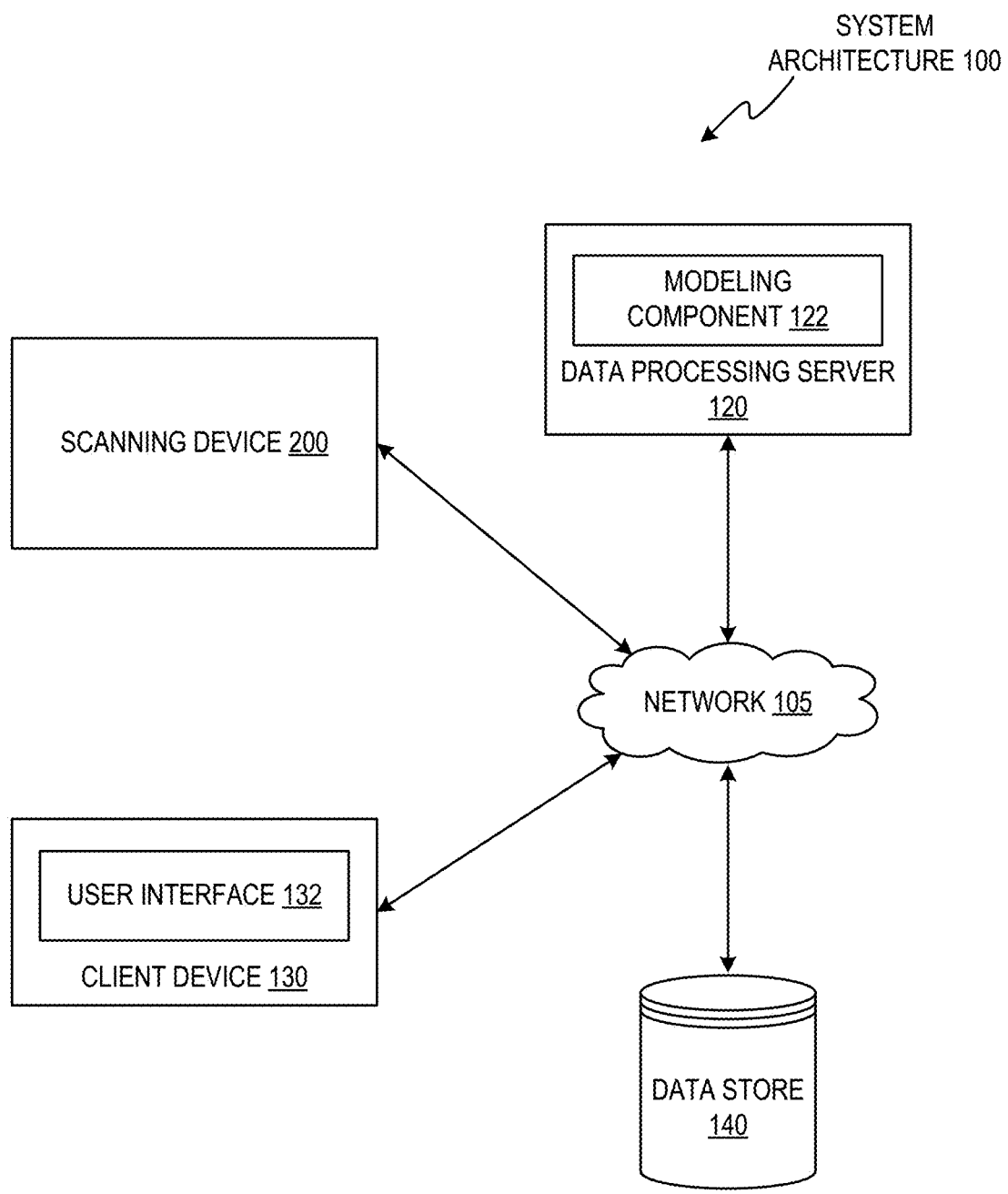
FIG. 1 illustrates an exemplary system architecture in accordance with embodiments of the present disclosure.

Exemplary implementations of the embodiments of the present disclosure are now described. FIG. 1 illustrates an exemplary system architecture 100, in accordance with embodiments of the present disclosure. The system architecture 100 includes a scanning device 200, a data processing server 120, a client device 130, and a data store 140, with each device of the system architecture 100 being communicatively coupled via a network 105. One or more of the devices of the system architecture 100 may be implemented using a generalized computer system 600, described with respect to FIG. 6. The devices of the system architecture 100 are merely illustrative, and it is to be understood that other scanning devices, user devices, data processing servers, data stores, and networks may be present.

In one embodiment, network 105 may include a public network (e.g., the Internet), a private network (e.g., a local area network (LAN) or wide area network (WAN)), a wired network (e.g., Ethernet network), a wireless network (e.g., an 802.11 network or a Wi-Fi network), a cellular network (e.g., a Long Term Evolution (LTE) network), routers, hubs, switches, server computers, and/or a combination thereof. Although the network 105 is depicted as a single network, the network 105 may include one or more networks operating as stand-alone networks or in cooperation with each other. The network 105 may utilize one or more protocols of one or more devices to which they are communicatively coupled.

In one embodiment, the scanning device 200 includes a support base comprising substantially flat upper and lower surfaces, a pressure panel disposed on the upper surface of the support base, and a plurality of cameras distributed around an outer perimeter of the support base and substantially oriented toward a center of the pressure panel. In at least one embodiment, the scanning device 200 further comprises an on-board processing device operatively coupled to the pressure panel and each of the plurality of cameras. The processing device may be configured to activate and receive data generated by the pressure panel and each of the plurality of cameras. The scanning device 200 is described in greater detail with respect to FIGS. 2A-2C.

In one embodiment, the data processing server 120 may include one or more computing devices (such as a rackmount server, a router computer, a server computer, a personal computer, a mainframe computer, a laptop computer, a tablet computer, a desktop computer, etc.), data stores (e.g., hard disks, memories, databases), networks, software components, and/or hardware components from which digital contents may be retrieved. In at least one embodiment, the data processing server 120 may be a server utilized by the scanning device 200, for example, to process generated scan data of an individual's anatomy. In at least one embodiment, additional data processing servers may be present. In at least one embodiment, the data processing server 120 utilizes a modeling component 122 to generate and reconstruct 3D model data from data received from the scanning device 200, the functionality of which is described in greater detail with respect to FIG. 5.

In one embodiment, the client device 130 may include a computing device such as a personal computer (PC), laptop, mobile phone, smart phone, tablet computer, netbook computer, etc. An individual user may be associated with (e.g., own and/or operate) the client device 130. As used herein, a "user" may be represented as a single individual. However, other embodiments of the present disclosure encompass a "user" being an entity controlled by a set of users and/or an automated source. For example, a set of individual users federated as a community in a company or government organization may be considered a "user." In at least one embodiment, the user is the individual who is the subject of scanning by the scanning device 200. In at least one embodiment, the user is an operator, technician, or physician who is conducting or assisting with the scan of another individual with the scanning device 200.

The client device 130 may utilize one or more local data stores, which may be internal or external devices, and may each include one or more of a short-term memory (e.g., random access memory), a cache, a drive (e.g., a hard drive), a flash drive, a database system, or another type of component or device capable of storing data. The local data stores may also include multiple storage components (e.g., multiple drives or multiple databases) that may also span multiple computing devices (e.g., multiple server computers). In at least one embodiment, the local data stores may be used for data back-up or archival purposes.

The client device 130 may implement a user interface 132, which may allow the client device 130 to send/receive information to/from other client devices, the scanning device 200, the data processing server 120, and the data store 140. The user interface 132 may be a graphical user interface (GUI). For example, the user interface 132 may be a web browser interface that can access, retrieve, present, and/or navigate content (e.g., web pages such as Hyper Text Markup Language (HTML) pages) provided by the data processing server 120. In one embodiment, the user interface 132 may be a standalone application (e.g., a mobile "app," etc.), that enables a user to use the client device 130 to send/receive information to/from other client devices, the scanning device 200, the data processing server 120, and the data store 140.

In one embodiment, the data store 140 may include one or more of a short-term memory (e.g., random access memory), a cache, a drive (e.g., a hard drive), a flash drive, a database system, or another type of component or device capable of storing data. The data store 140 may also include multiple storage components (e.g., multiple drives or multiple databases) that may also span multiple computing devices (e.g., multiple server computers). In at least one embodiment, the data store 140 may be cloud-based. One or more of the devices of system architecture 100 may utilize their own storage and/or the data store 140 to store public and private data, and the data store 140 may be configured to provide secure storage for private data. Such private data may include, for example, data descriptive of individuals who have been scanned with the scanning device 200, including names, contact information, physiological data, and scan data. In at least one embodiment, the data store 140 may be used for data back-up or archival purposes.

Although each of the scanning device 200, the data processing server 120, the client device 130, and the data store 140 are depicted in FIG. 1 as single, disparate components, these components may be implemented together in a single device or networked in various combinations of multiple different devices that operate together. In at least one embodiment, some or all of the functionality of the data processing server 120 and/or the data store 140 may be performed by the scanning device 200, the client device 130, or other devices. In an exemplary embodiment, the client device 130 may be within close proximity of or integrated with the scanning device 200, for example, as part of a scanning kiosk. In such embodiments, the client device 130 may implement the functionality of the modeling component 122, or may utilize the data processing server 120 to implement some or all of the functionality of the modeling component 122.

Scanning Device Embodiments

Figure 2A:
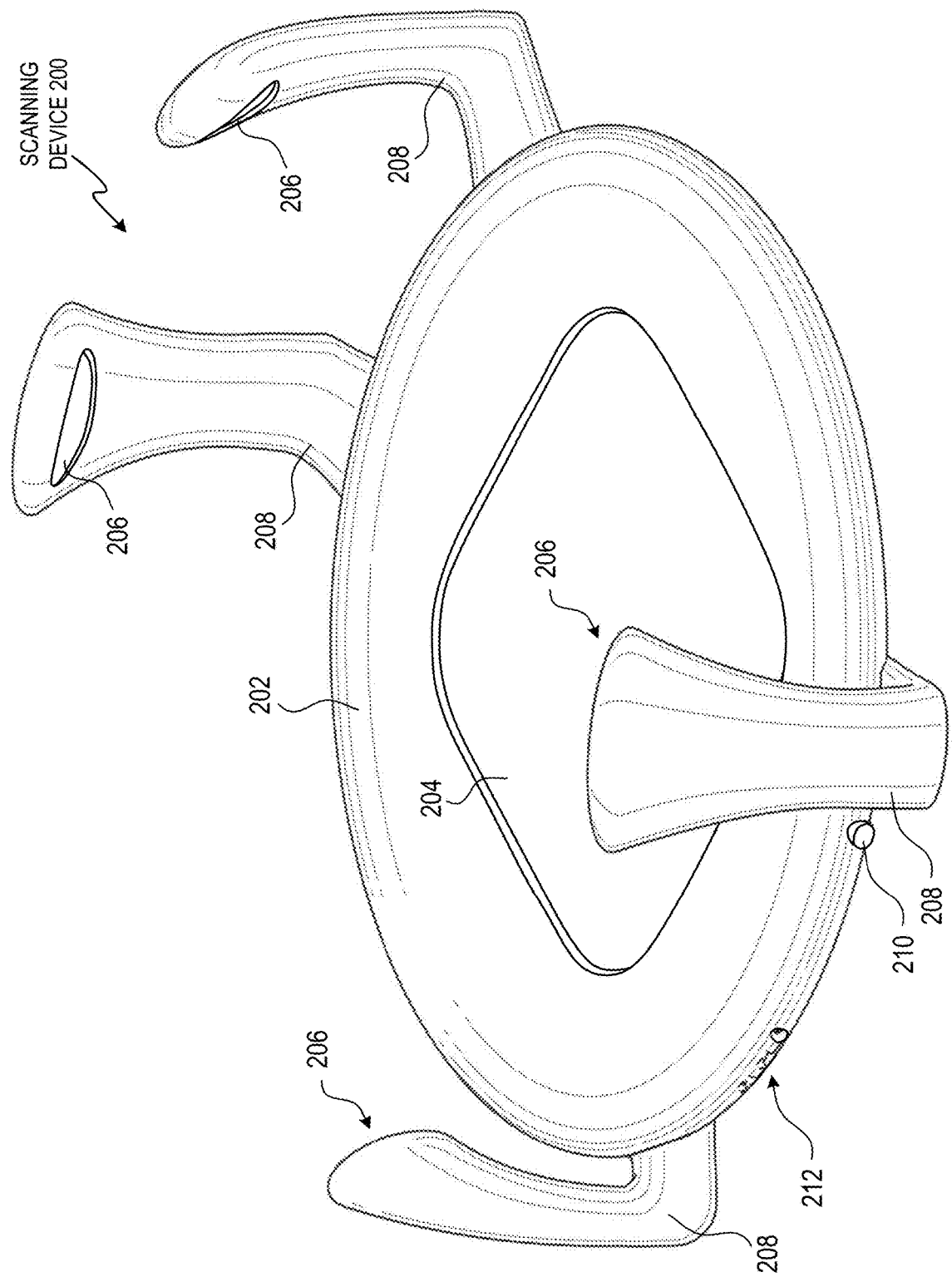
FIG. 2A shows a perspective view of an exemplary scanning device in accordance with embodiments of the present disclosure.
Figure 2B:
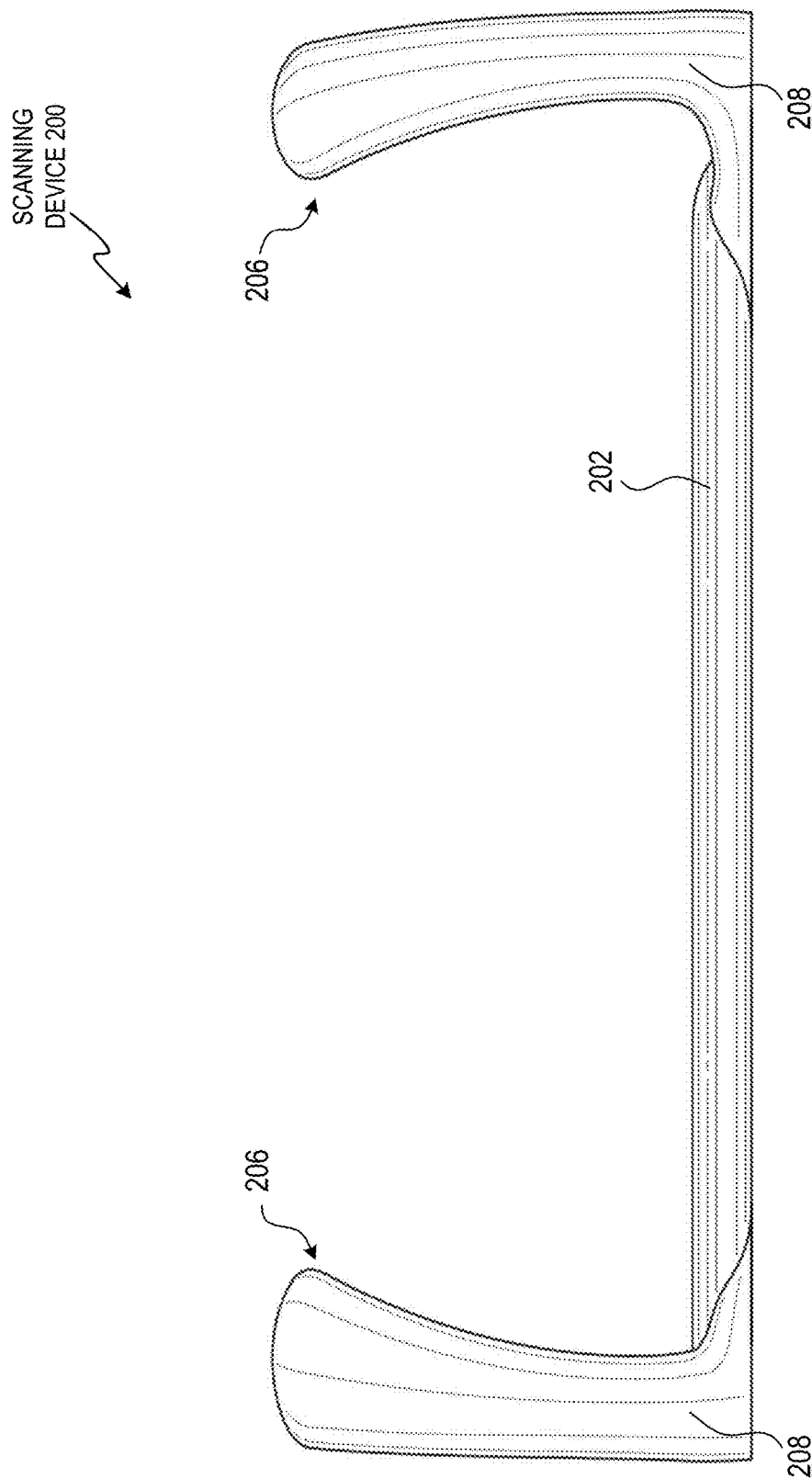
FIG. 2B shows a side view of the exemplary scanning device in accordance with embodiments of the present disclosure.

FIGS. 2A-2C show various views of the exemplary scanning device 200 in accordance with embodiments of the present disclosure. The scanning device 200 includes a support base 202, a pressure panel 204, and a plurality of cameras 206 distributed around the support base 202. Each camera 206 may be configured for capturing high-definition images (e.g., individual images or a movie), and may, in at least one embodiment, comprise an infrared sensor for capturing depth data. In at least one embodiment, one or more of the cameras 206 may be a stereo depth camera. The scanning device 200 may have one or more on-board processing devices that are operatively coupled to the cameras 206 and the pressure panel 204, and may transmit activation signals to the various components and control the timing at which signals are captured, collected, and transmitted to one or more external devices for processing (e.g., the data processing server 120, the client device 130, etc.).

In at least one embodiment, one or more of the cameras 206 are housed within or mechanically coupled to respective support arms 208. Each of the cameras 206 are mechanically coupled to or integrally formed with the support base via support arms 208, which may be substantially L-shaped, rigid members. In at least one embodiment, one or more of the support arms 208 are fixed in place, resulting in fixed, unmovable positions for the cameras 206. This may be beneficial in optimizing angles and distances at which images of the foot or feet are captured. In at least one embodiment, the positions of each camera 206 may be adjusted along the perimeter of the support base 202. For example, one or more of the support arms 208 may extend radially from the support base 202, and/or may be rotatable around a central axis of the support base 202 (e.g., slideably coupled to a track underneath the support base 202) and adjusted to a particular azimuthal angle. In at least one embodiment, one or more of the support arms 208 may be telescoping in order to adjust the vertical positions of their respective cameras 206 with respect to the support base 202.

In at least one embodiment, the cameras 206 may be positioned to define a walking path 214 across the support base 202, as illustrated in FIG. 2C. In the top view of FIG. 2C, the left-most and right-most support arms 208 may be horizontally separated by a distance (e.g., 24-36 inches) to allow for the individual to walk onto the support base 202 and pressure panel 204 either to enter the scanning device and prepare for a static scan, or to perform dynamic gait analysis. For example, to perform a static scan of both feet, the user may enter the scanning device from the bottom of FIG. 2C and rotate their feet/body by about 90 degrees. In at least one embodiment, the cameras 206 may be further separated to define an additional walking path (e.g., a walking path orthogonal to the walking path 214).

In at least one embodiment, the cameras 206 may be configured to rotate around the outer perimeter of the support base 202 to perform image capture at different angles with respect to the user's foot or feet. The scanning device 200 may include a motorized coupling mechanism that allows the support arms 208 to travel along a stationary track, or each of the support arms 208 may be coupled to a motorized track. The one or more cameras can be controlled such that images of the foot are captured at different angles as the cameras 206 traverse the track. In at least one embodiment, fewer than all of the cameras 206 shown are utilized, such as two or three cameras.

In at least one embodiment, the pressure panel 204 includes a plurality of pressure cells arranged in a planar configuration (e.g., arranged in rows and columns or in another arrangement) adapted for generating polychromatic foot pressure readings. In at least one embodiment, the pressure panel may be an iStep® Pressure Plate (Aetrex Worldwide, Inc.) or a variation thereof, which uses over 3,700 pressure sensors that each span an area of 0.25 $cm^2$. A method of generating a customized insole for footwear using information obtained from a pressure map of an individual's feet is described in U.S. Pat. No. 7,493,230, the disclosure of which is hereby incorporated by reference herein in its entirety. Functionality for performing pressure measurements and capturing images of an individual's feet and processing the captured data may be utilized similar to the descriptions in U.S. Pat. Nos. 9,402,567, 10,417,772, 10,463,257, and 10,492,712, the disclosures of which are hereby incorporated by reference herein in their entireties.

In at least one embodiment, the support base 202 includes a power button/power indicator 210 for activating the scanning device 200. In at least one embodiment, the support base includes a panel 212, which may include a power input port and one or more ports for establishing a hard-wired connection with a client device (e.g., the client device 130) or a data processing server (e.g., the data processing server 120). In at least one embodiment, the scanning device 200 may be communicatively coupled to the client device or data processing server via a wireless connection.

In one embodiment, an exemplary process for performing a scan with the scanning device 200 comprises first performing a static scan of the individual's foot or feet. For example, the individual may be instructed (e.g., by a display screen operably coupled to the scanning device 200 or to an intermediate device, such as the client device 130 implementing the user interface 132) to step onto the pressure panel 204 with one foot or with both feet. In embodiments where the user steps onto the pressure panel 204 with one foot, the individual is then instructed to place the other foot by itself onto the pressure panel 204 after completion of a scan of the first foot. In at least one embodiment, the static scan comprises measuring an underfoot pressure of the individual's foot or feet by the pressure panel 204 and capturing images of and/or depth data for the individual's foot or feet by the cameras 206. After performing the static scan, the individual may be instructed to walk out of the scanning device 200 to perform a dynamic gait analysis by measuring a change in underfoot pressure over time during the individual's movement. In at least one embodiment, the user may be instructed to walk into and out of the scanning device 200, walk into the scanning device 200 and remain still, or walk out of the scanning device 200 from a static position. In at least one embodiment, the dynamic gait analysis is performed prior to performing the static scan.

Figure 3A:
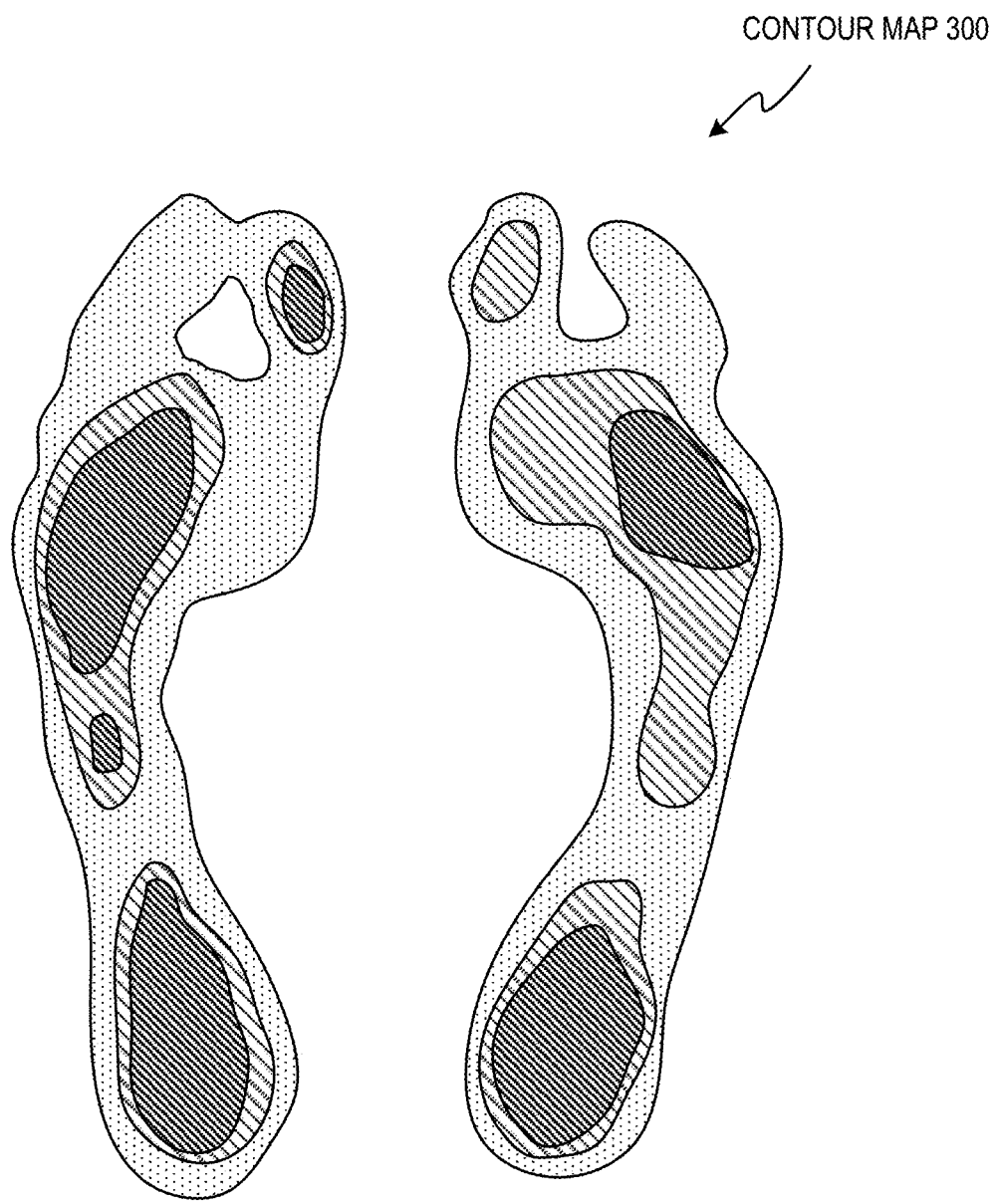
FIG. 3A shows an exemplary contour map of underfoot pressure presented by a user interface in accordance with embodiments of the present disclosure.
Figure 3B:
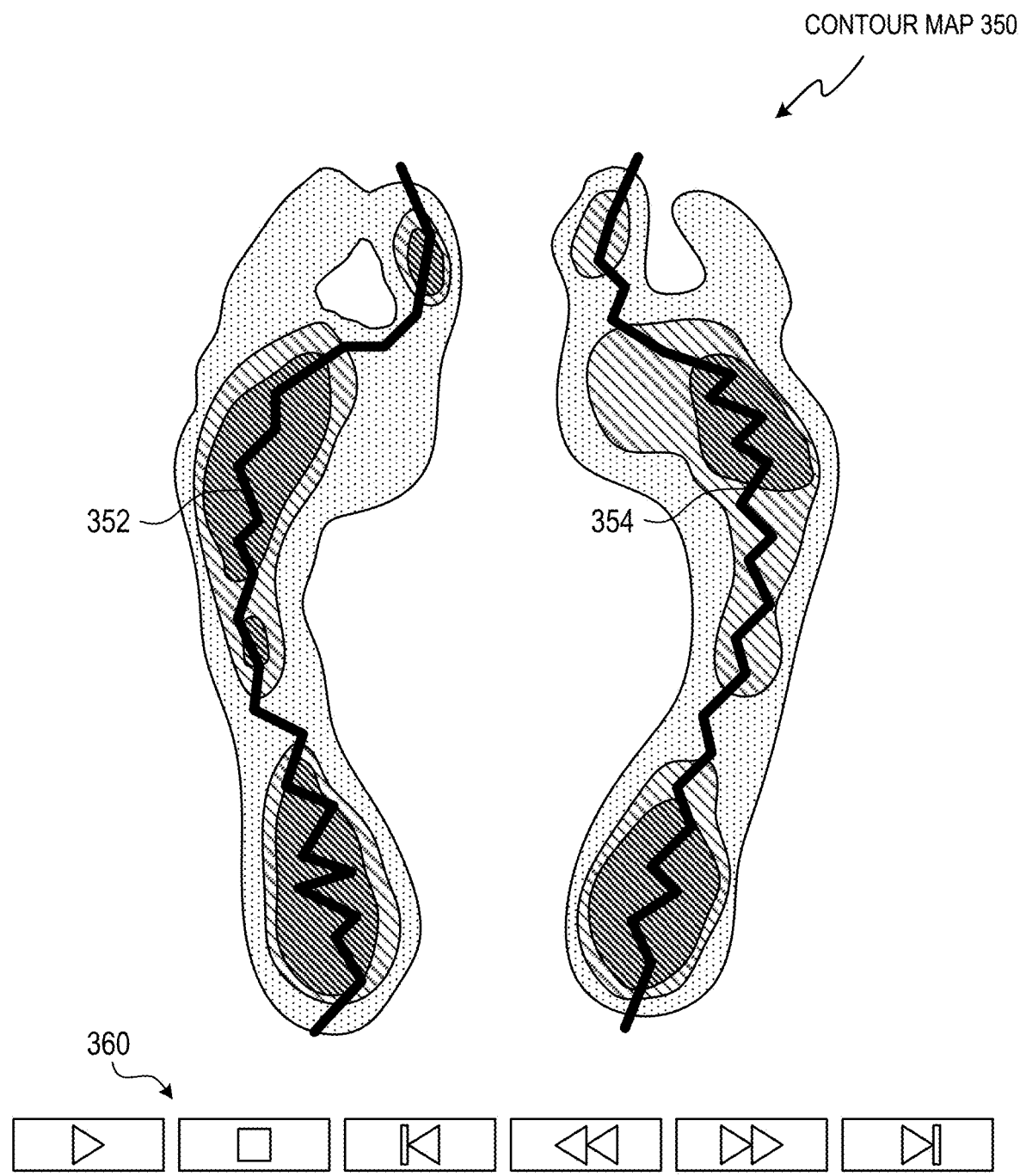
FIG. 3B shows an exemplary contour map of underfoot pressure as obtained from a dynamic gait analysis measurement in accordance with embodiments of the present disclosure.

FIGS. 3A and 3B show illustrative static or interactive display screens that may be presented for display by a display device that is operatively coupled to the scanning device 200 during and after a scan. For example, the client device 130 may utilize the user interface 132 to present the display screens. FIG. 3A shows a measurement of underfoot pressure in the form of a contour map 300 to show areas of low to high underfoot pressure, which is captured while performing a static scan of both of an individual's feet by a pressure panel. FIG. 3B shows a contour map 350 generated from a dynamic gait analysis measurement. The contour map 350 can correspond to a frame of a video generated from the measurement, with each frame corresponding to a time point at which underfoot pressure data was measured. Each frame may have overlaid thereon paths 352 and 354 that trace out maximum pressure over time as measured during the individual's step. In at least one embodiment, the user interface 132 provides playback options 360 to view the video.

Geometric Partial Differential Equations for Surface Evolution and Fitting

In at least one embodiment, the 3D shape of each foot, prior to a final meshing step is reconstructed in the form of a smooth (non-triangulated) 3D surface. In at least one embodiment, the data generated from the reconstruction may be used for the purpose of rendering and visualization. In at least one embodiment, the smooth 3D surface is represented implicitly as the zero-level iso-surface of a 3D scalar level-set function, which may be sampled discretely on a uniform Cartesian 3D grid. The 3D grid may represent a rectangular volume of 3D space within which both feet are positioned during image capture. Depth images may be captured from the cameras (e.g., the cameras 206), all of which are positioned outside the rectangular volume while pointing into the volume itself. The spacing between grid samples (voxels) may be selected as, for example, 3 millimeters (or another suitable spacing), although the zero-level iso-surface which represents the reconstructed foot may be computed and extracted at sub-voxel resolution via tri-linear interpolation between neighboring voxels.

In at least one embodiment, a coarse initial voxelized estimate of the foot in the form of a solid volume made up of grid voxels (a 3D binary mask) is obtained using depth carving methods, for example, by intersecting the depth hulls computed from each of the four calibrated depth cameras. An initial estimate of the model may be computed quickly, however, in at least one embodiment, the model is volumetrically under-estimated as well as non-smooth due to the nature of depth carving methodologies in general. Once the initial carved estimate is obtained, it may be converted into an iso-surface representation by applying, for example, a signed distance transform to the binary mask. The resulting 3D signed distance function may serve a starting scalar level-set function which is evolved according to geometric partial differential equations (PDEs) discretized to match the structure of the uniform 3D grid.

Figure 4A:
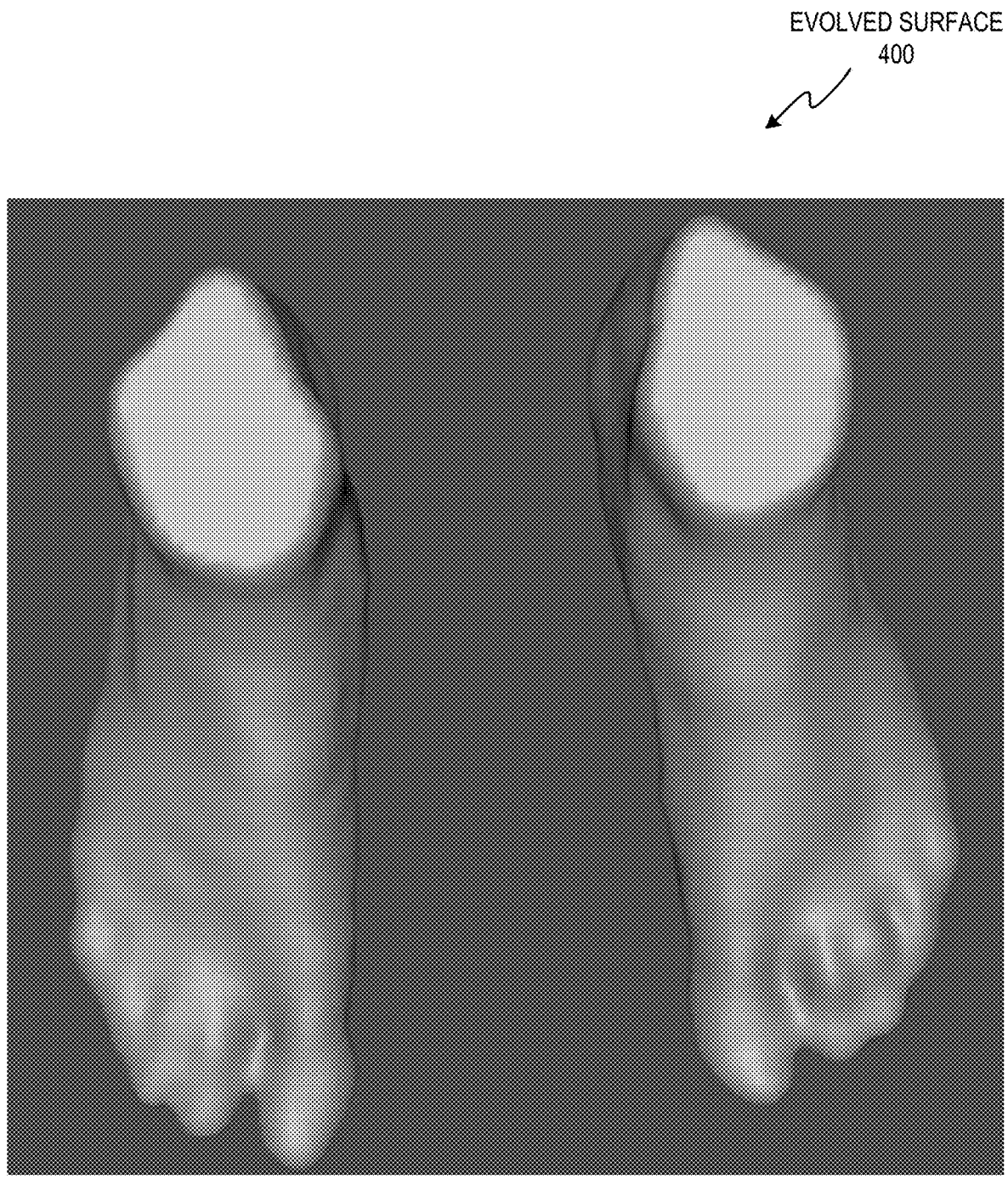
FIG. 4A shows top surfaces of 3D models of an individual's feet modeled by an evolution process utilizing depth images in accordance with embodiments of the present disclosure.
Figure 4B:
FIG. 4B shows bottom surfaces of 3D models of an individual's feet modeled by an evolution process utilizing underfoot pressure in combination with depth images in accordance with embodiments of the present disclosure.
Figure 4B:
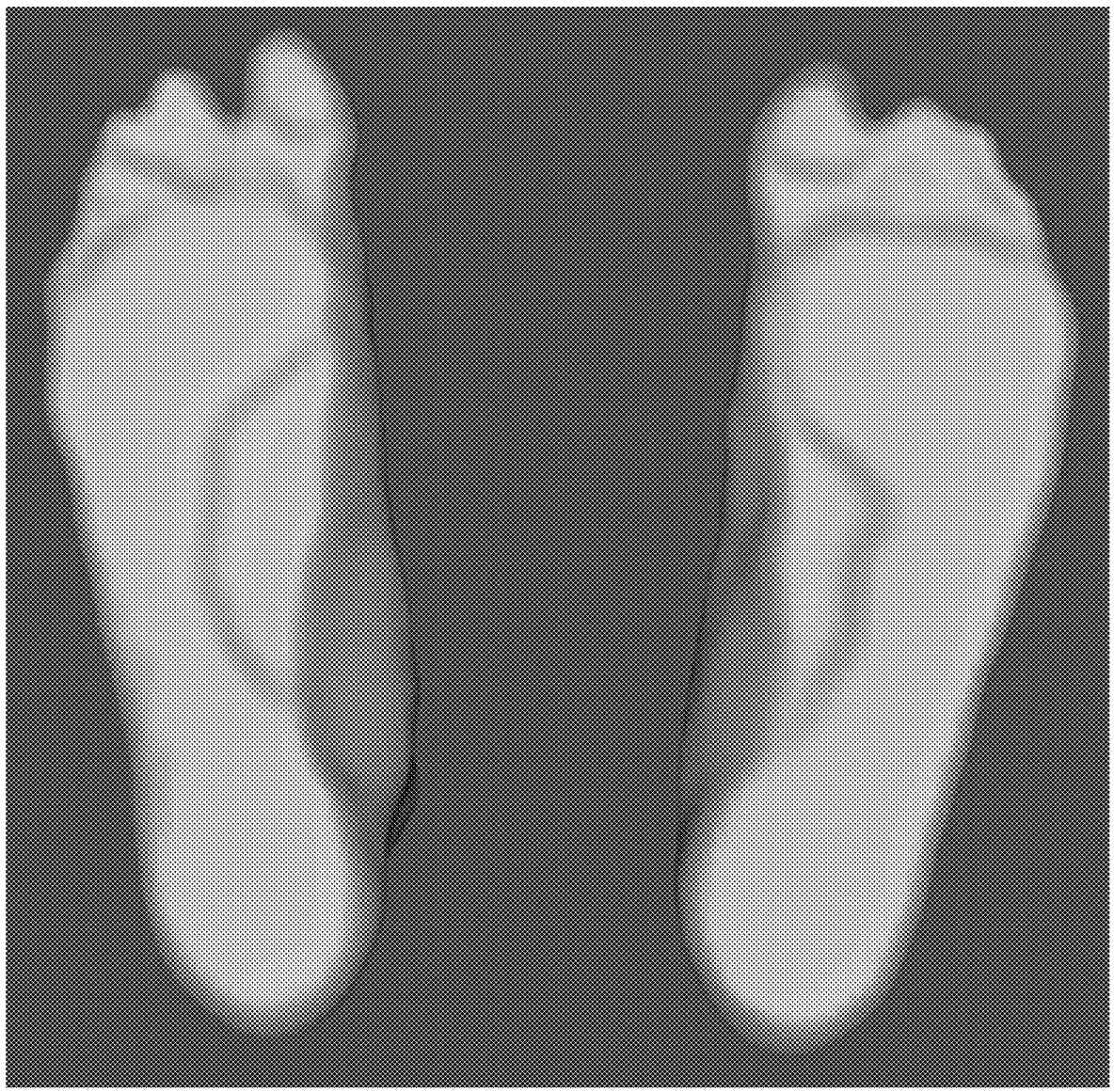

In at least one embodiment, the PDE evolution is calculated to most efficiently decrease a surface fitting score which minimizes the average depth between each surface point visible to a given camera and the depth value acquired at that same point by the same camera. The fitting score may also include a smoothness term which penalizes noisy, bumpy, or otherwise non-smooth structure. The trade-off between measured and reconstructed depth fidelity and smoothness may be tuned to obtain the desired level of smoothness along different portions of the reconstructed foot. In at least one embodiment, evolution occurs until the final shape of the foot converges to the best combination of smoothness and average depth mismatch across all of the cameras. Prior to discretization, the evolution may be computed according to a "gradient descent" PDE (described in detail below), while its final discrete implementation may take the form of an iterative explicit update of the discretized PDE via finite differences. FIG. 4A illustrates a 3D representation of upper portions of the individual's feet after surface evolution and fitting based on depth images of the feet.

An exemplary variational model for PDE-based foot reconstruction from depth images is now described in greater detail. The variational model utilizes back projection between each depth image, an estimated foreground surface S (the individual's foot or feet), and an estimated background plane B (the support base 202 or the pressure panel 204). A camera projection that maps a 3D point X into a corresponding two-dimensional (2D) pixel at location $u_i$ in the ith camera can be denoted as H. The mapping is unique in the forward direction (3D to 2D starting from point X), but may be ambiguous in the backward direction (2D to 3D starting from $u_i$) since there is an entire 3D ray which passes through the camera center and the associated image pixel $u_i$ (which can be treated as a 3D point within the focal plane of the ith camera). Tracking backwards along this ray starting from the camera until it intersects either the foreground surface S or background plane B, the first point of intersection can be defined to be the unique 3D back-projected point X associated with the camera image pixel $u_i$. The forward and backward camera projects can be denoted as $u_i=\Pi_i(X)$ and $X=\Pi_i^{-1}(u_i)$, respectively.

In at least one embodiment, given an estimated foreground surface S and background plane B, a ray-traced back-projection method can be used to define an estimated depth image value $\hat{d}_i$ for each camera pixel $u_i$. This can be performed by measuring a depth between each back-projected 3D point X and the camera center according to:

$$\hat{d}_i(u_i) = \text{depth}(\Pi_i^{-1}(u_i)).$$

In at least one embodiment, a weighted residual depth error may be formulated for each camera, with the weighting being by a function $h|\mathbb{R} \to \mathbb{R}$. This error may be implemented by penalizing the difference between measured depth image values $d_i$ and the back-projected depth values $\hat{d}_i$ according to:

$$E_i = \sum_{u_i} h(\hat{d}_i - d_i),$$

where $h \geq 0$ is chosen to be increasing for positive arguments and decreasing for negative arguments according to $$\begin{cases} h(x) > 0 & x > 0 \\ h(x) < 0 & x < 0 \end{cases}$$

such that the penalty always increases as the absolute value of the depth discrepancy grows (regardless of whether the discrepancy represents overestimation or underestimation).

In at least one embodiment, the continuous limit of the weighted residual depth error, as the resolution of the camera images increases, takes the form of an integral, which allows for a resolution-independent cost function to be expressed as:

$$E_i \to \int_{\Omega_i} h(\hat{d}_i - d_i) du_i.$$

In at least one embodiment, a continuum cost function (representing a fitting score) can be defined by summing over each depth image and adding a surface smoothness function that penalizes the surface area of the reconstructed surface S according to:

$$E = \sum_i \int_{\Omega_i} h(\hat{d}_i - d_i) du_i + \lambda \int_S dA,$$

where λ>0 is a weighting factor that can be tuned to balance a desired degree of smoothness with a desired agreement between the measured and reconstructed depth values $d_i$ and $\hat{d}_i$, respectively. The ability to naturally integrate depth discrepancy and smoothing into a single continuous error function is an important advantage of this approach, which helps to avoid various complications associated with traditional point-cloud stitching approaches to 3D surface reconstruction.

In at least one embodiment, a continuous PDE (e.g., gradient descent PDE) can be constructed to describe the evolution of the surface S which reduces the integrated cost function E as fast as possible. In at least one embodiment, the gradient descent PDE is calculated as:

$$\frac{\partial S}{\partial t} = \left( \frac{h(Z_i - d_i \circ \Pi_i) - h(b_i - d_i \circ \Pi_i)}{Z_i^3} X_i \cdot \nabla \chi_i + \chi_i \frac{\dot{h}(Z_i - d_i \circ \Pi_i)}{Z_i^2} + \lambda_\kappa \right) N,$$

where K denotes a unit normal to the surface, $\chi_i$ denotes a visibility indicator (0 or 1) for camera i, $X_i=(X_i, Y_i, Z_i)$ denotes the 3D point within the camera reference frame (rather than the inertial frame), $b_i$ denotes the background plane depth with respect to camera i, and N denotes the outward unit normal for the surface.

The gradient descent PDE is discretized using finite differences according to a chosen 3D grid resolution for the reconstructed surface, and can be iteratively evolved with a fixed number of explicit forward-Euler update steps applied to an initial voxelized depth-carved estimate of the foot surface. This allows for an improved sub-voxel estimate of the surface prior to final meshing and visualization.

A further advantage of the iterative PDE approach (beyond direct control of smoothness already discussed above) is the ability to also directly incorporate additional information about the underside of the foot, which is not visible to any of the four depth cameras, via a pressure map image obtained by sensors underneath a plate on which the foot rests (e.g., the pressure panel 204). In at least one embodiment, by choosing the bottom of the 3D Cartesian grid to correspond with the top of the plate, the reconstructed foot surface can be left open (in the form of a hole) along the higher pressure portions of the 3D grid boundary which correspond to the place of direct contact between the plate and the foot. The boundary of this hole can then be compared with the boundary of the 2D region which appears in the measured pressure map. The mismatch between these two boundaries can then be added to the surface fitting score, which will in turn change the behavior of the computed gradient descent PDE to now achieve not only a balance of matching average depth and surface smoothness, but of matching pressure boundary shape for the underside of the foot as well. The ability to blend all three of these factors without the appearance of artifacts in the final fitted 3D surface is a significant advantage of the PDE approach over alternative point cloud or finite element approaches.

Figure 5:
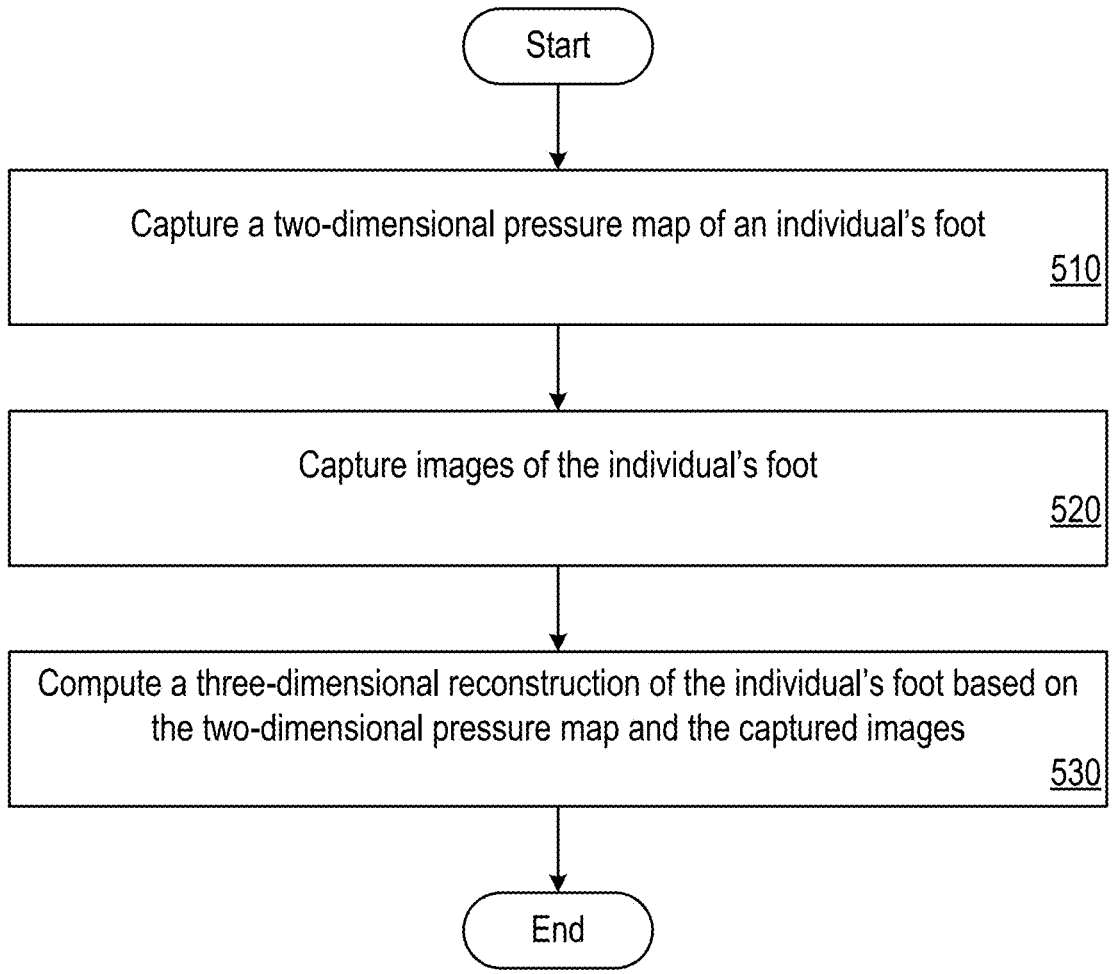
FIG. 5 is a flow diagram illustrating a method of scanning an individual's foot or feet in accordance with embodiments of the present disclosure.

FIG. 5 is a flow diagram illustrating a method 500 of scanning an individual's foot or feet in accordance with embodiments of the present disclosure. The method 500 may be performed by processing logic that includes hardware (e.g., circuitry, dedicated logic, programmable logic, microcode, etc.), software (e.g., instructions run on a processing device to perform hardware simulation), or a combination thereof. In at least one embodiment, the method 500 is performed by a processing device of the data processing server 120 implementing the modeling component 122, which transmits signals to the scanning device 200 to manage data capture. In at least one embodiment, some or all of the functionality of the modeling component 122 is distributed between the scanning device 200, the data processing server 120, and/or the client device 130.

The method 500 begins at block 510, where the processing device captures (e.g., directly by the scanning device 200 or by the scanning device 200 under the control of the data processing server 120) a two-dimensional pressure map of an individual's foot (or feet) while the individual is standing on a pressure panel (e.g., the pressure panel 204).

At block 520, the processing device captures images of the individual's foot (or feet) by a plurality of cameras (e.g., the cameras 206) arranged around the pressure panel. In at least one embodiment, the cameras are depth cameras that capture images comprising depth data. In some implementations, the processing device captures a series of two-dimensional pressure maps of the individual's foot as the individual steps onto and/or off of the pressure panel (e.g., a dynamic gait analysis measurement).

At block 530, the processing device computes a three-dimensional reconstruction of the individual's foot based on the two-dimensional pressure map and the captured images (e.g., as described herein with respect to the gradient descent PDE and related fitting score). In at least one embodiment, the processing device utilizes a PDE to evolve a surface representative of the individual's foot using depth data from the captured images by minimizing a fitting score, and applies a penalty to the fitting score based on a mismatch between a boundary of the two-dimensional pressure map and a boundary of the surface.

In at least one embodiment, the processing device generates data descriptive of an orthotic device based on the three-dimensional reconstruction of the individual's foot, for example, by generating a shape that matches an underfoot surface represented by the three-dimensional reconstruction. In at least one embodiment, the processing device generates a recommendation of a pre-made orthotic device based on various features represented by or derivable from the three-dimensional reconstruction (e.g., shoe size, arch height, heel width, or other features that would be appreciated by one of ordinary skill in the art). In at least one embodiment, the processing device transmits the data descriptive of the orthotic device to a manufacturing device to fabricate the orthotic device.

Exemplary Computer System Embodiments

Figure 6:
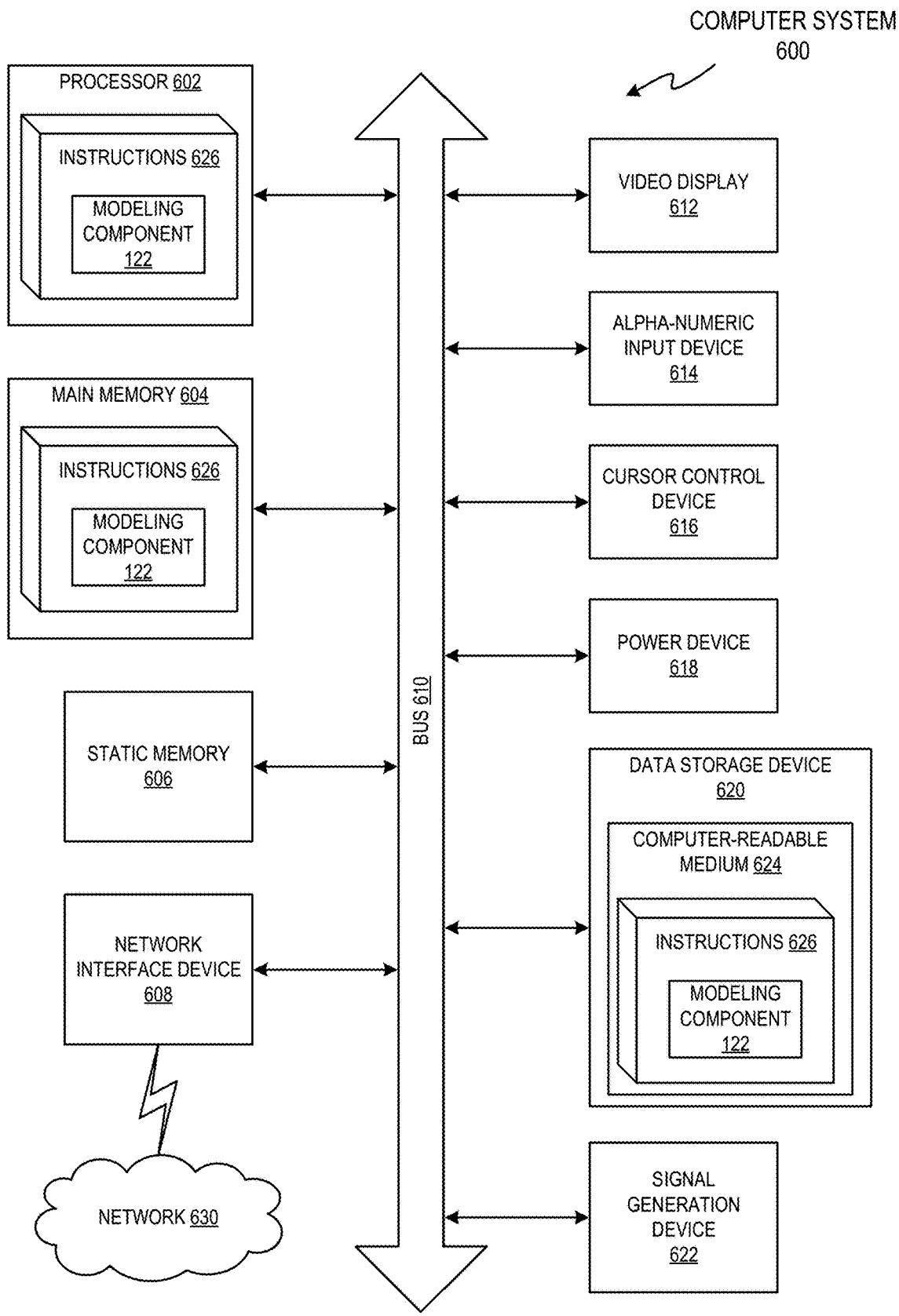
FIG. 6 is a block diagram illustrating an exemplary computer system for use in accordance with embodiments of the present disclosure.

FIG. 6 illustrates a diagrammatic representation of a machine in the exemplary form of a computer system 600 within which a set of instructions (e.g., for causing the machine to perform any one or more of the methodologies discussed herein) may be executed. In alternative embodiments, the machine may be connected (e.g., networked) to other machines in a LAN, an intranet, an extranet, or the Internet. The machine may operate in the capacity of a server or a client machine in client-server network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein. Some or all of the components of the computer system 600 may be utilized by or illustrative of at least some of the devices of the system architecture 100, such as the scanning device 200, the data processing server 120, the client device 130, and the data store 140.

The exemplary computer system 600 includes a processing device (processor) 602, a main memory 604 (e.g., read-only memory (ROM), flash memory, dynamic random access memory (DRAM) such as synchronous DRAM (SDRAM) or Rambus DRAM (RDRAM), etc.), a static memory 606 (e.g., flash memory, static random access memory (SRAM), etc.), and a data storage device 620, which communicate with each other via a bus 610.

Processor 602 represents one or more general-purpose processing devices such as a microprocessor, central processing unit, or the like. More particularly, the processor 602 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processor 602 may also be one or more special-purpose processing devices such as an ASIC, a field programmable gate array (FPGA), a digital signal processor (DSP), network processor, or the like. The processor 602 is configured to execute instructions 626 for performing the operations and steps discussed herein, such as operations associated with the modeling component 122.

The computer system 600 may further include a network interface device 608. The computer system 600 also may include a video display unit 612 (e.g., a liquid crystal display (LCD), a cathode ray tube (CRT), or a touch screen), an alphanumeric input device 614 (e.g., a keyboard), a cursor control device 616 (e.g., a mouse), and/or a signal generation device 622 (e.g., a speaker).

Power device 618 may monitor a power level of a battery used to power the computer system 600 or one or more of its components. The power device 618 may provide one or more interfaces to provide an indication of a power level, a time window remaining prior to shutdown of computer system 600 or one or more of its components, a power consumption rate, an indicator of whether computer system is utilizing an external power source or battery power, and other power related information. In at least one embodiment, indications related to the power device 618 may be accessible remotely (e.g., accessible to a remote back-up management module via a network connection). In at least one embodiment, a battery utilized by the power device 618 may be an uninterruptable power supply (UPS) local to or remote from computer system 600. In such embodiments, the power device 618 may provide information about a power level of the UPS.

The data storage device 620 may include a computer-readable storage medium 624 on which is stored one or more sets of instructions 626 (e.g., software) embodying any one or more of the methodologies or functions described herein. The instructions 626 may also reside, completely or at least partially, within the main memory 604 and/or within the processor 602 during execution thereof by the computer system 600, the main memory 604 and the processor 602 also constituting computer-readable storage media. The instructions 626 may further be transmitted or received over a network 630 (e.g., the network 105) via the network interface device 608.

In one embodiment, the instructions 626 include instructions for operating or processing data generated by the scanning device 200, as described throughout this disclosure. While the computer-readable storage medium 624 is shown in an exemplary embodiment to be a single medium, the terms "computer-readable storage medium" or "machine-readable storage medium" should be taken to include a single medium or multiple media (e.g., a centralized or distributed database, and/or associated caches and servers) that store the one or more sets of instructions. The terms "computer-readable storage medium" or "machine-readable storage medium" shall also be taken to include any transitory or non-transitory medium that is capable of storing, encoding or carrying a set of instructions for execution by the machine and that cause the machine to perform any one or more of the methodologies of the present disclosure. The term "computer-readable storage medium" shall accordingly be taken to include, but not be limited to, solid-state memories, optical media, and magnetic media.

In the foregoing description, numerous details are set forth. It will be apparent, however, to one of ordinary skill in the art having the benefit of this disclosure, that the present disclosure may be practiced without these specific details. In some instances, well-known structures and devices are shown in block diagram form, rather than in detail, in order to avoid obscuring the present disclosure.

Some portions of the detailed description may have been presented in terms of algorithms and symbolic representations of operations on data bits within a computer memory. These algorithmic descriptions and representations are the means used by those skilled in the data processing arts to most effectively convey the substance of their work to others skilled in the art. An algorithm is herein, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the preceding discussion, it is appreciated that throughout the description, discussions utilizing terms such as "configuring," "receiving," "converting," "causing," "streaming," "applying," "masking," "displaying," "retrieving," "transmitting," "computing," "generating," "adding," "subtracting," "multiplying," "dividing," "selecting," "parsing," "optimizing," "calibrating," "detecting," "storing," "performing," "analyzing," "determining," "enabling," "identifying," "modifying," "transforming," "aggregating," "extracting," "running," "scheduling," "processing," "capturing," "evolving," "fitting," or the like, refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices.

The disclosure also relates to an apparatus, device, or system for performing the operations herein. This apparatus, device, or system may be specially constructed for the required purposes, or it may include a general purpose computer selectively activated or reconfigured by a computer program stored in the computer. Such a computer program may be stored in a computer-or machine-readable storage medium, such as, but not limited to, any type of disk including floppy disks, optical disks, compact disk read-only memories (CD-ROMs), and magnetic-optical disks, read-only memories (ROMs), random access memories (RAMs), EPROMs, EEPROMs, magnetic or optical cards, or any type of media suitable for storing electronic instructions.

The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or." That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Reference throughout this specification to "certain embodiments," "one embodiment," "at least one embodiment," or the like means that a particular feature, structure, or characteristic described in connection with the embodiment is included in at least one embodiment. Thus, the appearances of the phrase "certain embodiments," "one embodiment," "at least one embodiment," or the like in various places throughout this specification are not necessarily all referring to the same embodiment.

The present disclosure is not to be limited in scope by the specific embodiments described herein. Indeed, other various embodiments of and modifications to the present disclosure, in addition to those described herein, will be apparent to those of ordinary skill in the art from the description and accompanying drawings. Thus, such other embodiments and modifications are intended to fall within the scope of the present disclosure. Further, while the present disclosure has been described in the context of a particular embodiment in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein, along with the full scope of equivalents to which such claims are entitled.

What is claimed is:

1. A scanning device comprising:
 a support base comprising substantially flat upper and lower surfaces;
 a pressure panel disposed on the upper surface of the support base, the pressure panel comprising a plurality of pressure sensors;
 a plurality of cameras distributed around an outer perimeter of the support base and substantially oriented toward a center of the pressure panel; and
 a processing device operatively coupled to the pressure panel and each of the plurality of cameras, wherein the processing device is configured to activate and receive data generated by the pressure panel and each of the plurality of cameras while an individual's foot is positioned on the pressure panel, wherein the processing device computes a three-dimensional reconstruction of the individual's foot in a form of a smooth three-dimensional surface comprising an upper portion and a lower portion, wherein the upper portion is computed based on images captured by the plurality of cameras, and wherein the lower portion is computed based on a two-dimensional pressure map captured by the pressure panel to account for the underside of the individual's foot that is not visible to the plurality of cameras.

2. The scanning device of claim 1, wherein the plurality of cameras disposed around the outer perimeter of the support base are equidistant from the center of the pressure panel.

3. The scanning device of claim 1, wherein the outer perimeter of the support base is a circular perimeter.

4. The scanning device of claim 3, wherein a total number of the plurality of cameras is four.

5. The scanning device of claim 4, wherein the four cameras are unevenly distributed around the circular perimeter.

6. The scanning device of claim 5, wherein a first distance between a first camera and a second camera is equal to a second distance between a third camera and a fourth camera, and wherein a third distance between the first camera and the third camera is less than a fourth distance between the second camera and the fourth camera.

7. The scanning device of claim 3, wherein the cameras are positioned to define a walking path through a center region of the scanning device.

8. The scanning device of claim 1, wherein at least one of the plurality of cameras comprises a depth sensor configured to capture depth data during image capture by its corresponding camera.

9. The scanning device of claim 1, wherein the pressure sensors of the plurality of pressure sensors are arranged in a planar configuration.

10. The scanning device of claim 9, wherein each of the plurality of pressure sensors, when the pressure panel is activated, are configured to generate signals representative of underfoot pressure when an individual's foot is in contact with the pressure panel, the signals collectively defining a two-dimensional pressure map of the individual's foot.

11. The scanning device of claim 1, wherein the processing device is configured to generate a three-dimensional reconstruction of an individual's foot based on data captured by the pressure panel and each of the plurality of cameras when the individual's foot is in contact with the pressure panel.

12. The scanning device of claim 1, wherein the processing device is configured to transmit data generated by the pressure panel and each of the plurality of cameras to a processing server for generating a three-dimensional reconstruction of the individual's foot and/or data descriptive of an orthotic device customized to the individual's anatomy.

13. The scanning device of claim 1, wherein the processing device is configured to capture dynamic gait data of an individual's foot as the individual steps onto and/or off of the pressure panel.

14. A method comprising:
capturing a two-dimensional pressure map of an individual's foot while the individual is standing on a pressure panel, the pressure panel comprising a plurality of pressure sensors;
capturing images of the individual's foot by a plurality of cameras arranged around the pressure panel; and
computing a three-dimensional reconstruction of the individual's foot
in a form of a smooth three-dimensional surface comprising an upper portion and a lower portion, wherein the upper portion is computed based on the captured images, and wherein the lower portion is computed based on the two-dimensional pressure map to account for the underside of the individual's foot that is not visible to the plurality of cameras; wherein computing the three-dimensional reconstruction of the individual's foot comprises:
utilizing a partial differential equation (PDE) to evolve a surface representative of the individual's foot using depth data from the captured images by minimizing a fitting score; and
applying a penalty to the fitting score based on a mismatch between a boundary of the two-dimensional pressure map and a boundary of the surface.

15. The method of claim 14, further comprising:
capturing a series of two-dimensional pressure maps of the individual's foot as the individual steps onto and/or off of the pressure panel.

16. The method of claim 14, further comprising:
generating data descriptive of an orthotic device based on the three-dimensional reconstruction of the individual's foot; and
transmitting the data descriptive of the orthotic device to a manufacturing device to fabricate the orthotic device.

17. A scanning device comprising:
a support base comprising substantially a flat upper surface and lower surfaces;
a plurality of cameras distributed around an outer perimeter of the support base and mechanically coupled thereto, wherein the plurality of cameras are configured to rotate around a central axis of the support base while remaining oriented toward a center of the support base,
a pressure panel disposed on the flat upper surface of the support base, wherein the scanning device is operatively coupled to the pressure panel and is configured to activate and receive data generated by the pressure panel; and
a processing device operatively coupled to each of the plurality of cameras, wherein the processing device is configured to activate and receive data generated by each of the plurality of cameras while an individual's foot is positioned on the pressure panel, wherein the processing device is further configured to compute a three-dimensional reconstruction of the individual's foot in a form of a smooth three-dimensional surface comprising an upper portion and a lower portion, wherein the upper portion is computed based on images captured by the plurality of cameras, and wherein the lower portion is computed based on a two-dimensional pressure map to account for the underside of the individual's foot that is not visible to the plurality of cameras.

18. The scanning device of claim 17, wherein the processing device is configured to cause the plurality of cameras to capture images while rotating around the outer perimeter of the support base.

* * * * *